United States Patent [19]

Close et al.

[11] 4,115,466
[45] Sep. 19, 1978

[54] SYNTHESIS OF ACETYLENIC COMPOUNDS USEFUL IN PREPARING DEHYDROPHYTOLS AND VITAMIN E

[75] Inventors: Ralph E. Close, Jacksonville, Fla.; William Oroshnik, Plainfield, N.J.

[73] Assignee: SCM Corporation, New York, N.Y.

[21] Appl. No.: 839,962

[22] Filed: Oct. 6, 1977

Related U.S. Application Data

[60] Continuation-in-part of Ser. No. 622,972, Oct. 16, 1975, abandoned, which is a division of Ser. No. 560,550, Mar. 20, 1975, Pat. No. 4,055,575.

[51] Int. Cl.[2] .................. C07C 11/28; C07C 11/22; C07C 5/22
[52] U.S. Cl. .................. 260/678; 260/666.5; 260/668 R; 260/668 A; 260/675.5; 260/677 XA; 260/680 R; 260/683.2; 260/683.65
[58] Field of Search .................. 260/678, 675.5

[56] References Cited

U.S. PATENT DOCUMENTS

| | | | |
|---|---|---|---|
| 2,207,070 | 7/1940 | Reppe et al. | 260/680 R |
| 2,207,071 | 7/1940 | Reppe et al. | 260/680 R |
| 2,210,828 | 8/1940 | Auerhahn et al. | 260/680 R |
| 2,325,398 | 7/1943 | Hearne et al. | 260/680 R |
| 3,166,605 | 1/1965 | Wotiz et al. | 260/678 |
| 3,369,054 | 2/1968 | Zelinski et al. | 260/678 |
| 3,567,794 | 3/1971 | Eberly | 260/680 XA |
| 3,671,605 | 6/1972 | Smith | 260/678 |

OTHER PUBLICATIONS

Johnson "The Chemistry of the Acetylenic Compounds" vol. II, p. 45 (1950), Arnold and Co.
Hennion et al., J. Am. Chem. Soc. 71, 1964–1966 (1949).
Jacobs et al., J. Am Chem. Soc. 77, 6254–6258 (1955).
Crandall et al., J. Organic Chem. 33, 3655–3657 (1968).

*Primary Examiner*—Delbert E. Gantz
*Assistant Examiner*—G. E. Schmitkons
*Attorney, Agent, or Firm*—Richard H. Thomas

[57] ABSTRACT

A process for the synthesis of an acetylenic hydrocarbon from an acetylenic carbinol which involves first replacing the hydroxyl group of the carbinol with a halogen to form a propargylic halide, dehalogenating the propargylic halide to form an allene, and isomerizing said allene to the desired acetylene. The present invention is particularly useful in the synthesis of Vitamin E.

9 Claims, 1 Drawing Figure

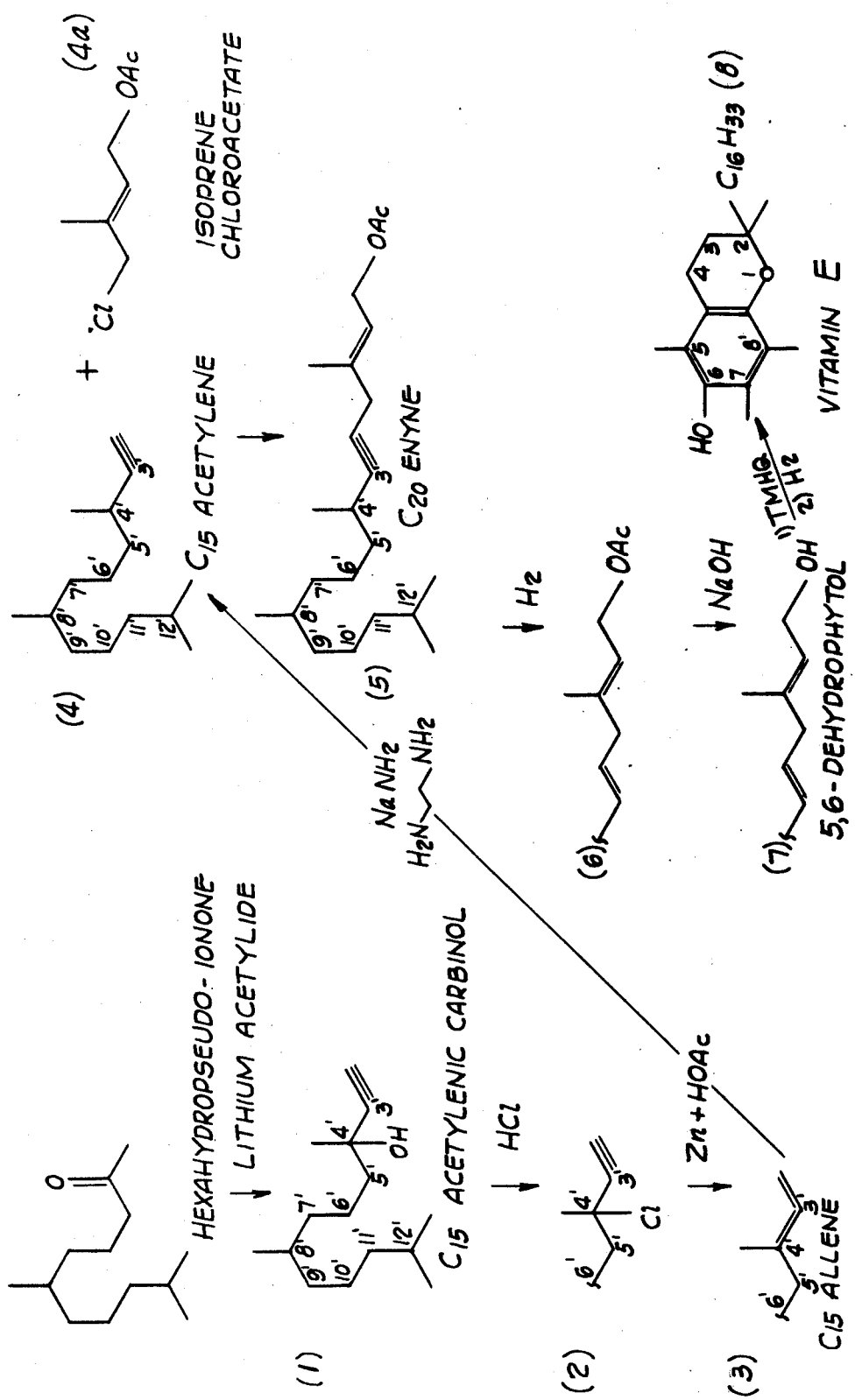

SYNTHESIS OF ACETYLENIC COMPOUNDS USEFUL IN PREPARING DEHYDROPHYTOLS AND VITAMIN E

This application is a continuation-in-part of prior application Ser. No. 622,972, filed Oct. 16, 1975 now abandoned; which application in turn was a division of application Ser. No. 560,550, filed Mar. 20, 1975 now U.S. Pat. No. 4,055,575.

The present invention relates to the preparation of acetylenic hydrocarbons from acetylenic carbinols; and in particular to a step in the synthesis of dehydrophytol (3,7,11,15-tetramethylhexadeca-2,5-dien-1-ol) and the production of Vitamin E therefrom.

BACKGROUND OF THE INVENTION

The synthesis of Vitamin E, that is, alpha-tocopherol (5,7,8-trimethyltocol) in the past has been accomplished primarily by reacting trimethylhydroquinone (TMHQ) with isophytol (3,7,11,15-tetramethylhexadec-1-en-3-ol) or phytol (3,7,11,15-tetramethylhexadec-2-en-1-ol) in a condensation reaction. The reaction is well known and has been practiced for many years.

The various routes to phytol and isophytol have been reviewed by Stalla-Bourdillon, *Ind. Chim. Belg.*, 35, 13 (1970); and also in "The Vitamins", Vol. 5, pages 168-223, Academic Press, New York, 1967. With few exceptions, these routes utilize a $C_{10}$ intermediate (natural or synthetic) and proceed to the $C_{20}$ phytol or isophytol by sequential addition of various carbon units ($C_4$ or less). The steps are numerous, and the syntheses are costly.

In copending application Ser. No. 353,215, filed Apr. 23, 1973, on "Synthesis of Vitamin A Intermediates and Conversion Thereof to Vitamin A", by William Oroshnik, now U.S. Pat. No. 3,949,006, a novel process is disclosed which comprises forming an ethynyl-terminated alkoxy-substituted beta-ionol intermediate from beta-ionone and then coupling such intermediate with a compound like "isoprene chloroacetate" (1-acetoxy-4-chloro-3-methylbut-2-ene) to produce a $C_{20}$ skeleton. The latter by semi-hydrogenation, hydrolysis and treatment with a strong base produced Vitamin A. The invention of copending application Ser. No. 353,215 (now U.S. Pat. No. 3,949,006) resides in part in the discovery that successful coupling of the intermediate and isoprene chloroacetate permitted elimination of at least one additional step in the Vitamin A synthesis. The present invention resides in part in the discovery that "isoprene chloroacetate" is also a useful reactant in the synthesis of Vitamin E.

SUMMARY OF THE INVENTION

The present invention resides in a process for the preparation of an acetylenic hydrocarbon from an acetylenic carbinol which involves first replacing the hydroxyl group of the carbinol with a halogen to form a propargylic halide, dehalogenating the propargylic halide to form an allene, and then isomerizing said allene to the desired acetylene. The present invention is particularly useful in the synthesis of dehydrophytol which in turn couples with trimethylhydroquinone to give dehydro-Vitamin E. This product on hydrogenation yields Vitamin E.

In a preferred embodiment, the present invention resides in a process for the synthesis of an acetylenic compound having the formula

wherein $R_4$ and $R_5$ are hydrogen, alkyl, aralkyl, alkenyl, alkadienyl, alkatrienyl and phenyl, comprising the steps of reacting an acetylenic carbinol having the formula

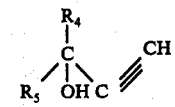

with a reagent capable of replacing the hydroxyl group with a halogen to produce a propargylic halide having the formula

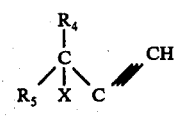

X being halogen; dehalogenating the propargylic halide forming an allene having the formula

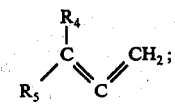

isomerizing said allene in the presence of a strong base to the acetylene of equation (1).

Preferably the dehalogenation of the propargylic halide is carried out by dissolving the halide in a mixture of glacial acetic acid and zinc dust. Also, in a preferred embodiment of the present invention, the isomerization is carried out by dissolving the allene in a solution of sodium amide in ethylene diamine.

For purposes of the present application, temperature is in degrees Centigrade and percentages are in terms of percentage by weight, unless otherwise specified.

BRIEF DESCRIPTION OF THE DRAWING

The invention may best be understood with reference to the accompanying drawing in which the FIGURE is a flow diagram illustrating a preferred process for the synthesis of Vitamin E in accordance with the present invention.

The process starts with the reaction of hexahydropseudo-ionone with a metal acetylide to form a hexahydropseudo-ionone derivative [formula (1)] having a terminal acetylene group and methyl and hydroxyl groups on the adjacent carbon atom. This compound in a series of novel steps is halogenated and then reacted with zinc and glacial acetic acid to form the corresponding allene [formula (3)], the latter being isomerized in a solution of sodamide in ethylene diamine and ether to form the $C_{15}$ acetylene compound represented by formula (4). Coupling with isoprene chloroacetate to form the basic $C_{20}$ enyne skeleton [formula (5)] is then carried out, for instance, following the teachings of copending application Ser. No. 353,215, now U.S. Pat. No. 3,949,006. Dehydrophytol (7) is obtained by the successive steps of partial hydrogenation of the acetylenic group, and saponification.

In the drawing and following examples, the numbers assigned to the various atoms of the formulae follow the conventional numbering system for tocopherols, both with regard to the product Vitamin E and intermediate compounds preceding Vitamin E. In other words, in the interest of facilitating understanding of the invention, each carbon atom of the intermediate compounds is given that number it will eventually have in the final alpha-tocopherol molecule. The numbering system for tocopherols can be found in *Methods in Enzymology,* Vol. XVIII, "Vitamins and Coenzymes", Part C, page 242, Donald B. McCormick and L. D. Wright, Academic Press (1971). This does not however apply to the naming of the compounds.

It is also understood that in the following formulae and equations, single bond lines attached to a carbon atom with no atom indicated represent the attachment of a methyl group to the atom.

EXAMPLE

Hexahydropseudo-ionone (note the FIGURE) is an available material produced by complete hydrogenation of the double bonds of pseudo-ionone, e.g., by catalytic hydrogenation. The hexahydropseudo-ionone is reacted with a metal acetylide such as lithium or sodium acetylide, in a known condensation reaction using conventional chemistry to provide 3,7,11-trimethyl-3-hydroxy-1-dodecyne (1), a $C_{15}$ acetylenic (ethynyl) carbinol compound having a terminal acetylene group and methyl and hydroxyl groups on the adjacent carbon atom. Again, the numbering system applied in the drawing for this formula and succeeding formulae follows the conventional numbering system for the tocopherols, each carbon atom being given the number it will eventually have in the alpha-tocopherol molecule.

A method for the preparation of compound (1) can be found in the publication, F. G. Fisher and K. Löwenberg, *Liebigs Ann. Chem.,* 475, 183 (1929). The subject matter of this publication is incorporated herein by reference. Specific pages of interest are pages 495 and 521.

Halogenation

The carbinol of formula (1) is converted to the corresponding chloride, 3,7,11-trimethyl-3-chloro-1-dodecyne (2) by dissolving the carbinol in a concentrated hydrochloric acid solution saturated with dry hydrogen chloride at about −25° to −10°. The conversion is carried out at −10° to 0°, under atmospheric pressure, preferably in the presence of cuprous chloride resulting in a substantially quantitative recovery of the chloride. The product, an acetylenic chloride or propargylic chloride, is a clean water-white oil.

In a particular example, 78.8 grams (0.351 mole) of the $C_{15}$ ethynylcarbinol is added at −25° to a mixture of 550 ml concentrated HCl and 18.5 grams of CuCl into which HCl gas has been bubbled until in excess. After warming to 0°–5° and at the end of a reaction period of about 2 hours, the reaction mixture was extracted with pentane and worked-up following conventional procedures to yield 87.3 grams of crude product.

The above reaction can be carried out with any hydrogen halide, e.g., hydrogen bromide, or following other procedures.

A Taylor publication, Chem. Rev., Vol. 67 (1967), discloses on page 319 the halogenation of an alcohol to obtain a halide. This is also disclosed in a Patai publication, *The Chemistry of Functional Groups. The Chemistry of the Hydroxyl Group. Part I.,* Interscience Pub. (1971), Chapter 11, "Displacement of Hydroxyl Groups", Brown, pages 593–631. The disclosure on pages 629 plus is especially pertinent. Similarly, this reaction is disclosed in a Whitmore et al publication, JACS, Vol. 55, page 361 (1933), *Tertiary Aliphatic Alcohols and Chlorides Containing Normal Butyl Groups.* Pages 363 plus of this publication are especially pertinent.

The subject matter of these publications is incorporated herein by reference.

Another procedure which may be employed in this step of the process is replacement of the hydroxyl group with a compound such as an alkyl or aryl sulfonate, such as disclosed in Crandall et al publication, J. Org. Chem., 33, 3655 (1968). This publication shows reductive removal of such an alkyl or aryl sulfonate employing lithium aluminum hydride. The methyl sulfonate or p-toluene sulfonate of the acetylenic carbinol of the present invention will undergo the same reduction in the presence of lithium aluminum hydride.

Dehalogenation to Allene (3)

The chloride of formula (2) is reductively dehalogenated to the corresponding $C_{15}$ allene, 3,7,11-trimethyl-dodeca-1,2-diene, by dissolving and stirring the chloride in a mixture of glacial acetic acid mixed with zinc dust, using the following proportions:

| | |
|---|---|
| $C_{15}$-Propargylic chloride* | 87.3 grams |
| Zinc dust (activated with dilute HCl) | 87.3 grams |
| HOAc (glacial) | 850 ml |

*The crude product from the halogenation step.

The reaction is exothermic but is carried out at room temperature by cooling, although this is not critical. Quenching in water after filtering off the unreacted zinc dust, taking up the oil precipitate with a solvent such as hexane, further washing, drying and concentrating, results in a crude product of 80% purity. This is then distilled at 0.5 mm pressure with very little or no polymerization to give a product of 84% purity. The yield of desired product was 85% of theoretical yield.

Although the above procedure employing glacial acetic acid and zinc dust is preferred, this dehalogenation/hydrogenation can also be carried out by a procedure disclosed in the above mentioned Taylor publication, page 325, column 1.

Rearrangement to $C_{15}$ Acetylene

Although there are many examples of basic reagents for bringing about the isomerization of allenes to acetylenes, a solution of sodium amide ($NaNH_2$) in ethylene diamine ($H_2N-CH_2-CH_2-NH_2$) produces an 87% by weight yield of distilled product of 70% purity. The bulk of the impurity is a conjungated diene.

The reaction is carried out by adding the allene dropwise to a solution of sodium amide ($NaNH_2$) in ethylene diamine-ether (30:70) maintained at room temperature. The reaction mixture is agitated during addition and for about 2 to 3 hours thereafter, followed by quenching with aqueous ammonium chloride and distillation.

The presence of the diene does not interfere in the subsequent coupling reaction of the acetylene with "isoprene chloroacetate" (1-acetoxy-4-chloro-3-methylbut-2-ene), as it is merely an inert component in the reaction mixture.

The resultant $C_{15}$ acetylene product is 3,7,11-trimethyldodeca-1-yne (4).

In a particular example, the following components were employed:

| | |
|---|---|
| $C_{15}$ allene* | 76.2 grams |
| Na | 13.5 grams |
| | (0.59 gram-atoms) |
| $NH_3$ | 700 ml |
| ether (anhydrous) | 700 ml. |
| $NH_2CH_2CH_2NH_2$ (dried over molecular sieves) | 280 ml |

* The crude product of dehalogenation step.

The ammonia and sodium are combined in the presence of a catalytic amount of $Fe(NO_3)_3.9H_2O$ at the boiling temperature of $NH_3$ to obtain a solution of $NaNH_2$ in liquid $NH_3$. The ether, ethylene diamine and allene are then added in that order. After a reaction period of about 4½ hours, quenching and work-up, 54.4 grams of distilled product (63.5% acetylene) was obtained.

A suitable procedure for carrying out this reaction is disclosed in the above mentioned Taylor publication, page 321. In addition, the reaction is disclosed in Bouis Ann. Chim. (10), 9, 459 (1928)—page 461, column 2.

Coupling Reaction to the Acetate of the $C_{20}$ Enyne

The compound of formula (4) is coupled with isoprene chloroacetate (1-acetoxy-4-chloro-3-methylbut-2-ene) (4a) to form the basic $C_{20}$ skeleton of dehydrophytol. The chloroacetate is known and prepared by the chlorohydrination of isoprene in glacial acetic acid as described in an article by W. Oroshnik and R. A. Mallory, *J. Amer. Chem. Soc.*, 72, 4608 (1950). It can be represented by the following formula:

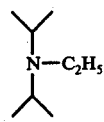
(4a)

Alternatively, the isoprene chloroacetate may be prepared by the method described in copending application Ser. No. 359,011, filed May 10, 1973, by Carlos G. Cardenas, now U.S. Pat. No. 4,001,307, assigned to assignee of the present application.

The coupling reaction results in the preparation of 3,7,11,15-tetramethyl-1-acetoxyhexadec-2-en-5-yne (5), a $C_{20}$ enyne.

The coupling reaction may be carried out employing several methods. The following methods are preferred.

Method A: This coupling reaction involves pre-forming a cuprous salt of the $C_{15}$ acetylene compound of formula (4) and then reacting the salt with the coupling reactant "isoprene chloroacetate" (4a) in an aprotic solvent such as dimethyl formamide (DMF). The cuprous salt is formed by reacting the $C_{15}$ acetylene compound with a Grignard reagent such as methyl magnesium chloride in the presence of tetrahydrofuran (THF) giving off methane as a gas to form an acetylenic Grignard compound and then adding cuprous chloride, copper replacing the magnesium chloride group. Following this, isoprene chloroacetate dissolved in DMF is added; and the tetrahydrofuran is driven off under vacuum leaving a DMF solution in which all the reactants are dissolved. This solution is heated for several hours at 80° C under nitrogen giving the $C_{20}$ enyne.

In a particular example, the following components were employed:

| | |
|---|---|
| $C_{15}$-acetylene (67.2% purity) | 9.9 grams (0.0317 mole) |
| Methyl-MgCl (1.25 M) | 27 ml (0.0388 mole) |
| CuCl | 3.52 grams (0.0356 mole) |
| THF (dry) | 11 + 25 = 36 ml |
| Isoprene Chloroacetate | 6.4 grams (0.0396 mole) |
| DMF | 35 ml |

The Grignard reagent was added dropwise to a solution of 11 ml of THF (tetrahydrofuran) and the acetylene at less than 30°, followed by warming to 60° and maintaining this temperature for 2 hours. This was followed by cooling, addition of CuCl, and addition of the chloroacetate with the remaining THF. The DMF is then added and the THF removed under vacuum heating up to 50°. The coupling reaction was carried out at about 90° for 6 hours, producing 3.0 grams of pure product (28% of theoretical yield).

Method B: An alternative method comprises forming a complex molecule of cuprous chloride and Honig's base

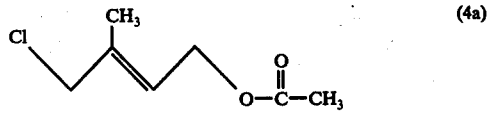

in DMF, the latter also having the $C_{15}$ acetylene compound dissolved therein. This forms the copper salt which is then reacted with "isoprene chloroacetate" (4a) as in Method A. Other aprotic solvents and combinations thereof can be employed. Also, other amines such as t-butyl amine can be employed. Yields of the $C_{20}$ enyne employing Method B are comparable to those employing Method A.

In this example, the following components were employed:

| | |
|---|---|
| $C_{15}$-acetylene | 20.6 grams |
| CuCl | 9.9 grams (0.10 mole) |
| Honig's Base | 14.2 grams (0.11 mole) |
| Isoprene Chloroacetate | 18.6 grams (0.115 mole) |
| DMF (dry) | 30 + 30 + 30 = 90 ml |

The base, CuCl and 30 ml DMF under nitrogen were mixed with the acetylene in an additional 30 ml of DMF, at about 45°. This mixture was heated to 50° and the chloroacetate in the remaining DMF was added. The reaction took place at 80°-85° for 6 hours. The yield was 14.1 grams of pure product or about 45% of theoretical.

Hydrogenation

The compound of formula (5) is next subjected to selective hydrogenation to convert the acetylenic bond to an ethylenic bond. This can be readily accomplished by a number of different catalysts, such as a nickel catalyst prepared from a nickel salt and $NaBH_4$, Lindlar catalyst, or 5% palladium on barium sulfate in the presence of quinoline. Selective semi-hydrogenation is commonplace, for instance as to conditions, amounts and procedures. In this particular example, the reaction was run at one atmosphere. Analyses by nuclear magnetic resonance and vapor phase chromatography showed the correct structure in good quantity.

The product obtained was 3,7,11,15-tetramethylhexadeca-2,5-dien-1-acetate (6), a $C_{20}$ dienol acetate.

Saponification of the $C_{20}$ Dienol Acetate to Dehydrophytol

The acetate of formula (6) is dissolved in 1–2% methanolic NaOH and allowed to stand for 12 hours at room temperature under nitrogen. The reaction mixture is then quenched with water, and the precipitated oil is taken up in hexane. The hexane solution after drying with anhydrous sodium sulfate or magnesium sulfate is concentrated under vacuum, and the residual oil can either be distilled under high vacuum or used as such in the subsequent steps. High yields of dehydrophytol [3,7,11,15-tetramethylhexadeca-2,5-dien-1-ol (7)] were obtained. UV absorption showed no detectable conjugation. The product was chromatographed on alumina, which gave a pure material.

Condensation of Dehydrophytol with TMHQ to Yield Dehydro-Vitamin E

For the synthesis of dehydro-Vitamin E, 0.45 grams (1.54 millimoles) dehydrophytol of formula (7) is reacted with 0.23 grams (1.51 millimoles) trimethylhydroquinone to yield dehydro-Vitamin E following the procedure published in the *Journal of Organic Chemistry*, Volume 36, (19) pages 2910–12 (1971), by Wehrli, Fryer and Metlesics. Essentially the method involves first forming a TMHQ—$BF_3$ complex in methylene chloride (2 ml) containing one equivalent of nitromethane (0.090 ml) and no excess $BF_3$, by bubbling in the $BF_3$ and precipitating the complex. The dehydrophytol is then added with 3.5 ml of methylene chloride at $-20°$ C; and the reaction is carried out for a period at $-20°$ C, then at $-10°$ C, and finally at room temperature to yield dehydro-Vitamin E.

The dehydro-Vitamin E obtained is hydrogenated with a platinum catalyst in methanol. Good yields of Vitamin E (8) (alpha-tocopherol) are obtained.

General Application of the Invention

The invention has been described with reference to the synthesis of dehydrophytol (7) employing hexahydropseudo-ionone as a starting material. Concepts of the invention are also applicable to the synthesis of perfume products and other intermediates such as dimethyloctanol and others. These products can be synthesized by coupling a reactant having the general formula:

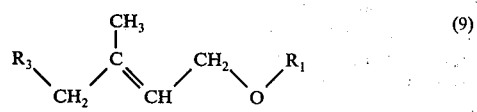

(9)

wherein $R_3$ is a halogen and $R_1$ is hydrogen or $COR_2$, $R_2$ being a lower alkyl, phenyl, substituted phenyl, or aralkyl with a second reactant derived from a starting compound of the general formula:

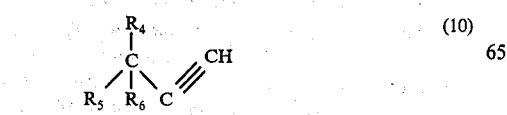

(10)

wherein $R_4$ and $R_5$ are hydrogen, alkyl, phenyl, substituted phenyl, aralkyl, alkenyl, alkadienyl and alkatrienyl, and $R_6$ is hydrogen.

Preferably $R_1$ is $COR_2$, $R_2$ is methyl, $R_4$ is methyl and $R_6$ is hydrogen, with $R_5$ being an alkyl, alkenyl, alkadienyl or alkatrienyl group such as any of the following:

Table 1

| | |
|---|---|
| 1) | methyl |
| 2) | 4-methylpentyl |
| 3) | 4,8-dimethyl-1,7-nonadienyl |
| 4) | 4,8-dimethyl-3,7-nonadienyl |
| 5) | 4,8-dimethyl-1,3-nonadienyl |
| 6) | 4,8-dimethyl-1-nonenyl |
| 7) | 4,8-dimethyl-3-nonenyl |
| 8) | 4,8-dimethyl-7-nonenyl |
| 9) | 4,8-dimethylnonyl |
| 10) | 4,8-dimethyl-1,3,7-nonatrienyl |

The products of the reaction will have the following general formula, $R_5$ being as previously defined:

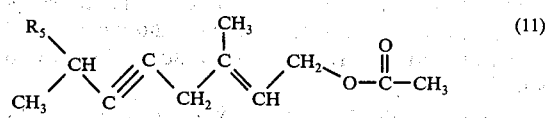

(11)

Selective partial or total hydrogenation and saponification of the reaction product then yields products with the following skeletons depending upon the structure of $R_5$.

Table 2

| $R_5$ Radical (from Table 1) | Skeleton of the Product |
|---|---|
| Group 1 | 3,7-dimethyloctanol |
| Group 2 | hexahydrofarnesol* |
| Groups 3–10 | dehydrophytol |

*3,7,11-trimethyldodecan-1-ol.

By the term "skeleton", it is meant that the reaction product may be 3,7-dimethyloctanol (or any of the others listed in the right-hand column of Table 2) if the hydrogenation is complete; or alternatively, the reaction product may have some unsaturated sites remaining while maintaining the same structure or arrangement of carbon atoms, if the hydrogenation is less complete.

Compounds of formula (10) can be made by the known reaction of ketones with the alkali metal salts of acetylenes, and specifically by the steps outlined above with reference to hexahydropseudo-ionone. For instance, to produce the compound of formula (10) with the $R_5$ radicals listed in Table 1, the following ketones could be used:

Table 3

| $R_5$ Radical | Ketone |
|---|---|
| methyl | acetone |
| 4-methylpentyl | 6-methylheptan-2-one |
| 4,8-dimethyl-3,7-nonadienyl | geranyl acetone |
| 4,8-dimethyl-1,3,7-nonatrienyl | pseudo-ionone |

Thus, in a specific example, acetone is reacted with a compound such as lithium acetylide to produce a $C_5$-acetylenic carbinol

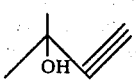

which, when reductively dehydroxylated by the reaction sequence used for going from the $C_{15}$-acetylenic carbinol to the $C_{15}$-acetylene, and coupled with isoprene chloroacetate, forms a basic $C_{10}$ skeleton capable of being hydrogenated and saponified to dimethyloctanol ($C_{10}H_{22}O$). Similarly, 6-methylheptan-2-one is reacted with lithium acetylide to produce a $C_{10}$ acetylenic carbinol having the formula:

 (12)

This compound when reductively dehydroxylated by the sequence described above and coupled with "isoprene chloroacetate" forms a basic $C_{15}$ skeleton capable of being hydrogenated and saponified to 3,7,11-trimethyldodecan-1-ol.

For purposes of the present application, the term "substituted phenyl" means substitution with hydrocarbon groups.

What is claimed is:

1. A process for the synthesis of an acetylenic compound having the formula

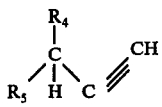 (1)

wherein $R_4$ and $R_5$ are hydrogen, alkyl, aralkyl, alkenyl, alkadienyl, alkatrienyl, phenyl and substituted phenyl, comprising the steps of
reacting an acetylenic carbinol having the formula

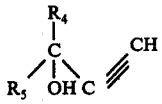 (2)

with a reagent capable of replacing the hydroxyl group with a radical X to produce a propargylic compound having the formula

 (3)

X being halogen, alkyl sulfonate, or aryl sulfonate; reductively removing said radical forming an allene having the formula

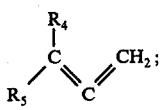 (4)

isomerizing said allene in the presence of a strong base to the acetylene of equation (1).

2. The process of claim 1 wherein said dehalogenation of the propargylic halide is carried out by dissolving said propargylic halide in a mixture of glacial acetic acid and zinc dust.

3. The process of claim 1 wherein $R_4$, $R_5$, or both, contain sites of unsaturation.

4. The process of claim 1 wherein $R_4$ is methyl, $R_5$ being methyl, 4-methylpentyl, 4,8-dimethyl-1,7-nonadienyl, 4,8-dimethyl-3,7-nonadienyl, 4,8-dimethyl-1,3-nonadienyl, 4,8-dimethyl-1-nonenyl, 4,8-dimethyl-3-nonenyl, 4,8-dimethyl-7-nonenyl, 4,8-dimethylnonyl, and 4,8-dimethyl-1,3,7-nonatrienyl.

5. The process of claim 1 wherein said carbinol is formed by reaction of a ketone and an alkali metal acetylide.

6. The process of claim 5 wherein said ketone is a compound selected from the group consisting of acetone, 6-methylheptan-2-one, geranyl acetone and pseudo-ionone.

7. A process for dehalogenating a propargylic halide having the general formula:

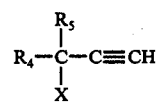 (1)

wherein $R_4$ and $R_5$ are hydrogen, alkyl, aralkyl, alkenyl, alkadienyl, alkatrienyl, substituted phenyl, or phenyl, X being a halogen, comprising the steps of:
a. dissolving said halide in a mixture of glacial acetic acid and zinc dust to form the corresponding allene having the formula:

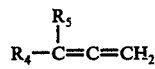

$R_4$ and $R_5$ being the same as in formula (1); and
b. isomerizing said allene to the corresponding acetylene.

8. The process of claim 7 wherein said isomerization is carried out by dissolving said allene in a solution of sodium amide in ethylene diamine.

9. A process for dehalogenation of a compound having a propargylic group of the configuration

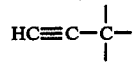

and a halogen, alkyl sulfonate or aryl sulfonate attached to the saturated carbon of the propargylic group, comprising the steps of;
a. dissolving said compound in a mixture of glacial acetic acid and zinc dust wherein the halogen, alkyl sulfonate or aryl sulfonate is reductively removed and the propargylic group is isomerized to an allene; and
b. isomerizing said allene back to the corresponding acetylene.

* * * * *

UNITED STATES PATENT AND TRADEMARK OFFICE
CERTIFICATE OF CORRECTION

PATENT NO. : 4,115,466
DATED : September 19, 1978
INVENTOR(S) : Ralph E. Close; William Oroshnik It is certified that error appears in the above-identified patent and that said Letters Patent are hereby corrected as shown below:

Column 6, line 5, in the Table, second line of the second column, change "(0.0388 mole)" to --(0.0338 mole)--.

Signed and Sealed this

Twelfth Day of December 1978

[SEAL]

Attest:

RUTH C. MASON
Attesting Officer

DONALD W. BANNER
Commissioner of Patents and Trademarks